US010635781B2

(12) United States Patent
Etchegoyen

(10) Patent No.: US 10,635,781 B2
(45) Date of Patent: *Apr. 28, 2020

(54) HEALTH ASSESSMENT BY REMOTE PHYSICAL EXAMINATION

(71) Applicant: UNILOC LUXEMBOURG S.A., Luxembourg (LU)

(72) Inventor: Craig S. Etchegoyen, Newport Beach, CA (US)

(73) Assignee: Uniloc 2017 LLC, Wilmington, DE (US)

(*) Notice: Subject to any disclaimer, the term of this patent is extended or adjusted under 35 U.S.C. 154(b) by 807 days.

This patent is subject to a terminal disclaimer.

(21) Appl. No.: 15/268,845

(22) Filed: Sep. 19, 2016

(65) Prior Publication Data
US 2017/0004272 A1 Jan. 5, 2017

Related U.S. Application Data

(63) Continuation of application No. 13/743,198, filed on Jan. 16, 2013, now Pat. No. 9,449,151.
(Continued)

(30) Foreign Application Priority Data

Apr. 24, 2012 (AU) ................. 2012100465

(51) Int. Cl.
G16H 40/40 (2018.01)
G06F 19/00 (2018.01)
(Continued)

(52) U.S. Cl.
CPC ......... *G06F 19/3418* (2013.01); *G06Q 50/22* (2013.01); *G16H 15/00* (2018.01)

(58) Field of Classification Search
CPC ................. A61N 1/08; G06F 17/30; G06F 19/30; G06F 19/32; G06F 19/321; G06F 19/324;
(Continued)

(56) References Cited

U.S. PATENT DOCUMENTS 5,682,526 A 10/1997 Smokoff et al.
5,715,451 A 2/1998 Marlin
(Continued)

FOREIGN PATENT DOCUMENTS

WO WO 2004/027676 4/2004
WO WO 2008/043341 4/2008
WO WO 2011/032605 3/2011

OTHER PUBLICATIONS

Corrigan, Elizabeth, Ph.D., "A Descriptive Analysis of Corporate Health Promotion Activity Evaluations" Texas Women's University, 1992.

Primary Examiner — Michael Tomaszewski
Assistant Examiner — William T. Monticello
(74) Attorney, Agent, or Firm — Sean D. Burdick

(57) ABSTRACT

A health assessment server allows people to conduct their own physical examinations using one or more medical measurement devices that are bound to one or more user devices. The user uses the medical measurement devices herself and submits the results to the health assessment server through a computer network such as the Internet, either directly from the medical measurement devices or through the user devices. The health assessment server determines an improved health state of the user at which benefits accrue to the user and periodically requests updated health attributes to measure progress toward the improved health state and projecting time until the improved health state is achieved.

14 Claims, 10 Drawing Sheets

Related U.S. Application Data

(60) Provisional application No. 61/602,461, filed on Feb. 23, 2012.

(51) Int. Cl.
  *G06Q 50/22* (2018.01)
  *G16H 15/00* (2018.01)

(58) Field of Classification Search
  CPC .... G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 10/10; G06Q 40/08; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00

See application file for complete search history.

(56) References Cited

U.S. PATENT DOCUMENTS

| | | |
|---|---|---|
| 8,635,087 B1 | 1/2014 | Igoe et al. |
| 9,449,151 B2 * | 9/2016 | Etchegoyen ........... G06Q 50/22 |
| 2003/0050537 A1 | 3/2003 | Wessel |
| 2004/0059599 A1 | 3/2004 | McIvor |
| 2006/0031094 A1 | 2/2006 | Cohen et al. |
| 2007/0180047 A1 | 8/2007 | Dong et al. |
| 2009/0037224 A1 * | 2/2009 | Raduchel ............... G06Q 50/24 705/3 |
| 2009/0146822 A1 | 6/2009 | Soliman |

\* cited by examiner

HEALTH ASSESSMENT BY REMOTE PHYSICAL EXAMINATION

This application is a continuation of U.S. application Ser. No. 13/743,198, filed Jan. 16, 2013, which claims priority to U.S. Provisional Application No. 61/602,461, which was filed Feb. 23, 2012, and which is fully incorporated herein by reference.

BACKGROUND OF THE INVENTION

1. Field of the Invention

The present invention relates generally to network-based computer services and, more particularly, to methods of and systems for conducting physical examination of a remotely-located person for the purposes of health assessment.

2. Description of the Related Art

Many types of insurance, e.g., life, health, and disability insurance, require physical examination of the insurance applicant. The premiums of such insurance ultimately offered depend upon actuarial analysis of characteristics of the applicant, such as demographics and health.

The physical examination is typically performed at the home or work place of the applicant, requiring travel by the person administering the examination. Such is expensive and limits the number of applicants an insurer can handle to those who can accommodate the travel schedule of such physical examiners. In addition, the types of information regarding the physical health of the applicant are limited to those that can be gathering during a brief visit, generally no more than an hour. Moreover, changes in the health of the applicant, once insured, are generally not assessed or only infrequently so.

What is needed is an automated and distributed health assessment system to assess and monitor the health of insured individuals.

SUMMARY OF THE INVENTION

In accordance with the present invention, a health assessment server allows people to conduct their own physical examinations using one or more medical measurement devices that are bound to one or more user devices under the control and operation of the people themselves. The health assessment server binds the medical measurement devices to user devices of a single human user and therethrough to the user. The user uses the medical measurement devices herself and submits the results to the health assessment server. The results can be used to determine insurance premium rates without requiring a visit from a human health examiner, resulting in great convenience and privacy for the user.

Examples of medical measurement devices include heart rate monitors, digital scales equipped with electronics for measuring body fat, blood glucose meters, and blood pressure monitors. Such medical measurement devices are intended to be self-administered and include a signal transducer and digital logic. Addition of communications logic allows the medical measurement devices to report health attributes of the user to the health assessment server through a computer network such as the Internet, either directly or through the user devices.

To discourage and detect fraud, the user devices collect log data contemporaneously with use of the medical measurement devices by the user. The log data can be photos or video from a web camera of the user device or can be operating system log data representing interaction between the user device and the medical measurement devices, including time stamps. The authenticity of the health attribute data can be determined by comparison of the photos or video to photo identification of the user, either manually or automatically with facial recognition logic, or by comparison of time stamps in the health attribute data to time stamps in the log data. Further authentication may be achieved using device fingerprinting technology with respect to the medical measurement devices themselves.

In addition to health assessment, the health assessment can motivate and assist in health maintenance or improvement of the user. The health assessment server determines an improved health state of the user at which benefits accrue to the user. For example, the health assessment server can use actuarial data to determine an improved health state of the user at which the user will pay lower insurance premiums, so that when certain milestones are achieved (such as a weight loss) the user will be rewarded with a corresponding reduction in her life insurance premium. As another example, the health assessment server can use actuarial data to determine an improved health state of the user at which the user will live significantly longer—e.g., if the user quits smoking, her life expectancy will be extended by some number of additional years, and this information may be communicated to or made available to the user.

The health assessment server then periodically requests updated health attribute of the user to measure progress toward the improved health state and projecting time until the improved health state is achieved.

BRIEF DESCRIPTION OF THE DRAWINGS

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. Component parts shown in the drawings are not necessarily to scale, and may be exaggerated to better illustrate the important features of the invention. In the drawings, like reference numerals may designate like parts throughout the different views, wherein:

DETAILED DESCRIPTION

Figure 1:
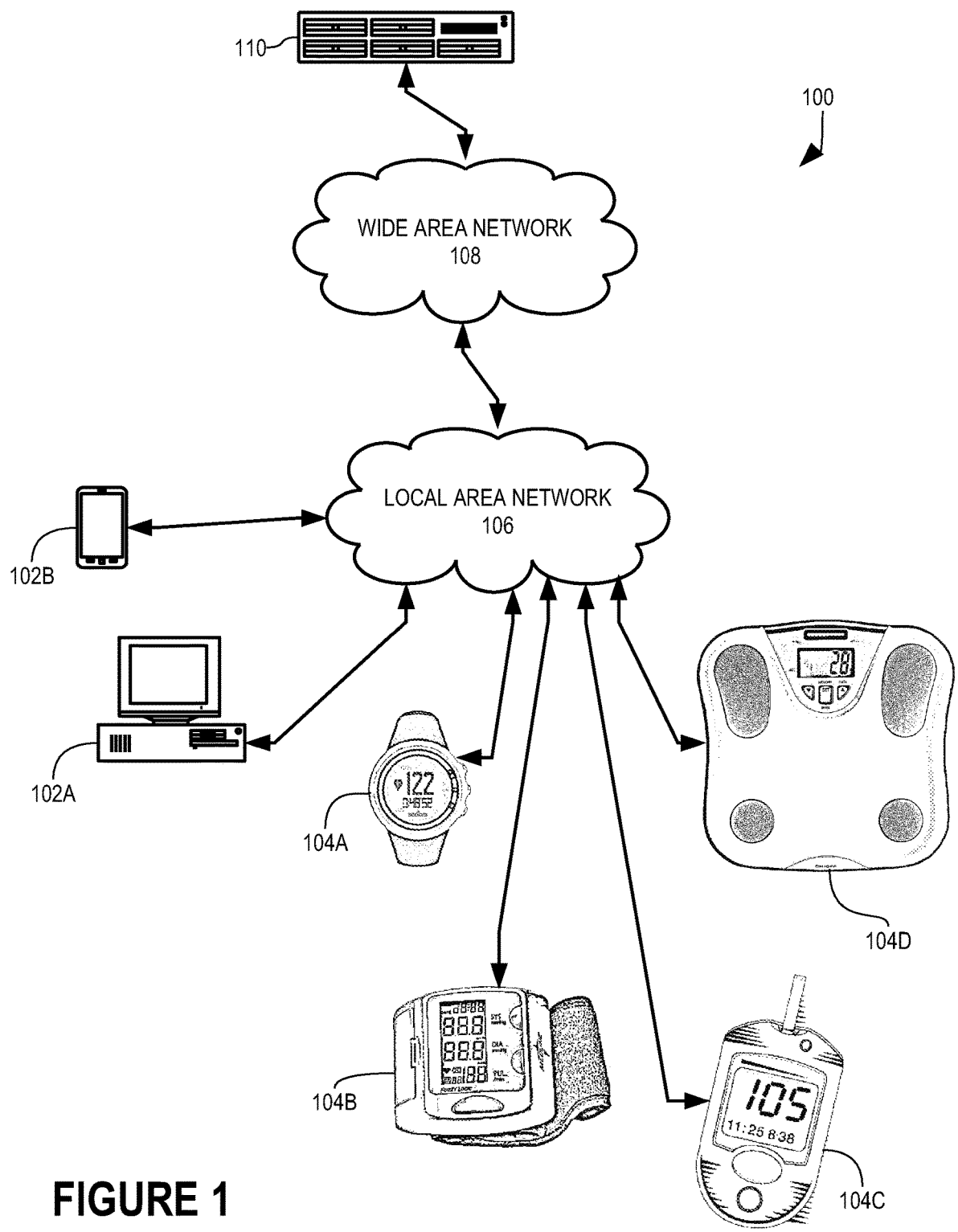
FIG. 1 is a diagram showing a health assessment server that cooperates through a wide area network with user devices and medical measurement devices to assess and monitor the health of a human user of the user devices in accordance with one embodiment of the present invention.

In accordance with the present invention, health assessment server 110 (FIG. 1) allows people to conduct their own physical examinations using one or more medical measurement devices 104A-D and one or more user devices 102A. In a manner described more completely below, health assessment server 110 binds medical measurement devices 104A-D to user devices 102A-B and therethrough to a single human user. Data from medical measurement devices 104A-D is sent through wide area network 108, which is the Internet in this illustrative embodiment, to health assessment server 110. Health assessment server 110 uses the data to assess the health of the user and to price an insurance policy for the user.

Figure 2:
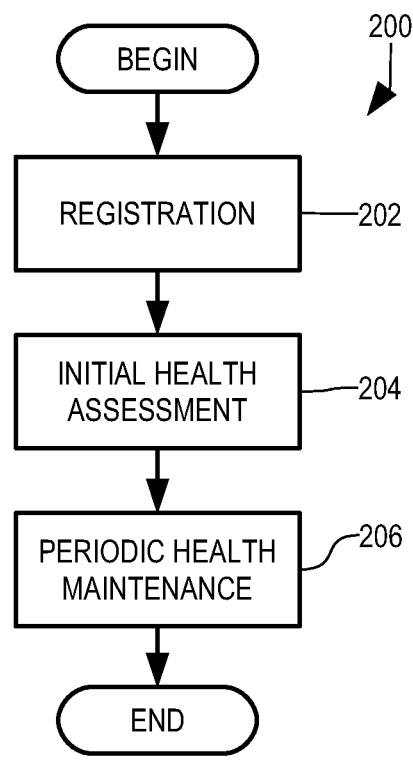
FIG. 2 is a logic diagram illustrating overall health assessment and maintenance in accordance with one embodiment of the invention.

Logic flow diagram 200 (FIG. 2) illustrates the overall process of health assessment and maintenance of the user's health by health assessment server 110.

In step 202, the user and one or more user devices 102A-B are registered with health assessment server 110. In step 204, health assessment server 110 coordinates with user devices 102A-B and one or more medical measurement devices 104A-D to perform an initial assessment of the user's health. In step 206, health assessment server 110 coordinates with user devices 102A-B and one or more medical measurement devices 104A-D to perform ongoing maintenance of the user's health.

Figure 3:
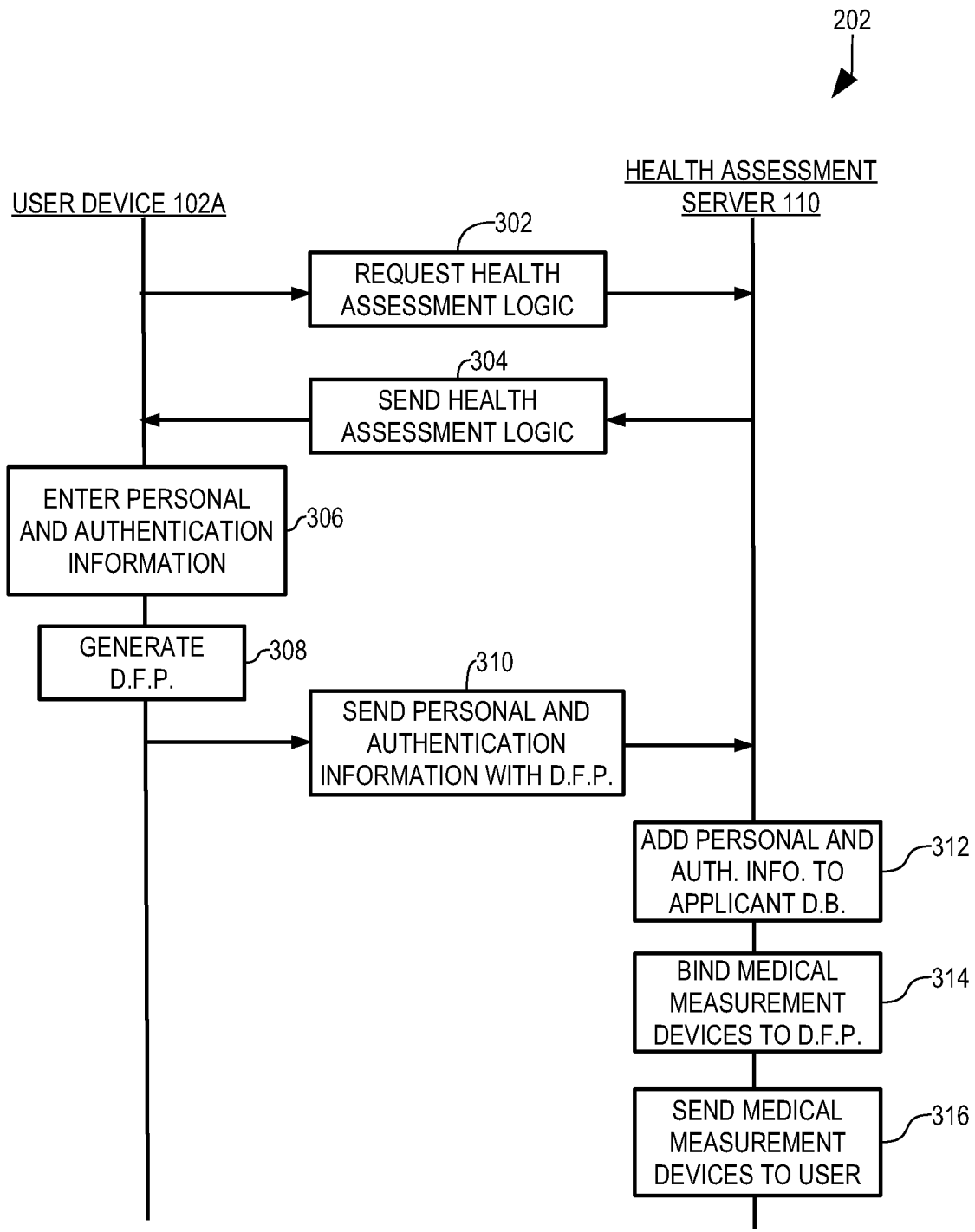
FIGS. 3, 4, and 5 are each a transaction flow diagram illustrating a step of the logic flow diagram of FIG. 2 in greater detail.

Step 202 is shown in greater detail as transaction flow diagram 202 (FIG. 3).

In step 302, the user causes a user device, e.g., user device 102A, to request health assessment logic from health assessment server 110. Herein, user devices 102A and 102B are analogous to one another and the description of user device 102A is equally applicable to user device 102B unless otherwise noted herein. In step 302, the user uses a conventional web browser and a URL (Uniform Resource Locater), and a user interface involving physical manipulation of one or more user input devices, to cause user device 102A to request the health assessment logic in this illustrative example.

In step 304, health assessment server 110 sends health assessment logic 620 (FIG. 6) in response to the request. Health assessment logic 620 can be a thin client in which the logic thereof executes within a web browser executing within client device 102A or can be a thick client requiring installation of health assessment logic 620 in the operating system of client device 102A.

In step 306, health assessment logic 620 of client device 102A provides a user interface by which the user enters personal and authentication information. The personal information can include personally identifying information such as the user's name and residential address and contact information, demographic data such as the user's height, weight, age, gender, and ethnicity, and health data such as the user's medical history and symptoms. The authentication data can include a username/password combination, a photo of or data from an identification card such as a driver's license, a photo of the user taken as the user enters the data, or health attribute data such as a fingerprint or retinal scan.

In step 308 (FIG. 3), health assessment logic 620 (FIG. 6) generates a digital fingerprint 640 of user device 102A. Digital fingerprints and their generation are known and are described, e.g., in U.S. Pat. No. 5,490,216 (sometimes referred to herein as the '216 patent), and in related U.S. Patent Application Publications 2007/0143073, 2007/0126550, 2011/0093920, and 2011/0093701 (the "related applications"), the descriptions of which are fully incorporated herein by reference. Digital fingerprint 640 is a unique identifier of user device 102A that is not easily spoofed or reverse engineered.

In step 310 (FIG. 3), health assessment logic 620 (FIG. 6) sends the personal and authentication data entered by the user and digital fingerprint 640 to health assessment server 110.

Figure 8:
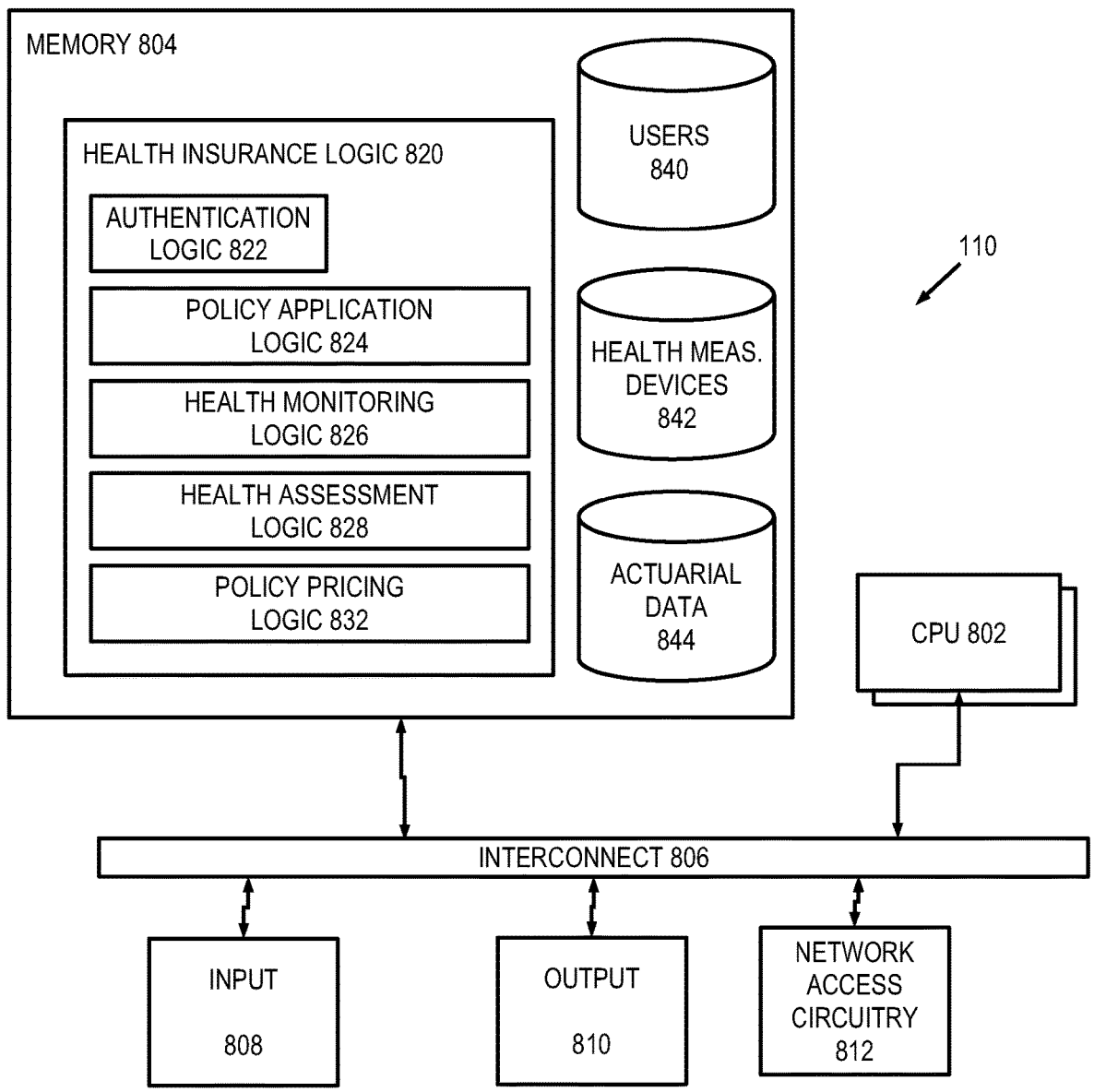
FIG. 8 is a block diagram showing the health assessment server of FIG. 1 in greater detail.

As shown in FIG. 8, health assessment server 110 includes health insurance logic 820, which in turn includes authentication logic 822, policy application logic 824, health monitoring logic 826, health assessment logic 828, and policy pricing logic 830. Policy application logic 824 specifies the items of information required from the user and entered in step 306 (FIG. 3) and responds to the information received in step 310.

Figure 9:
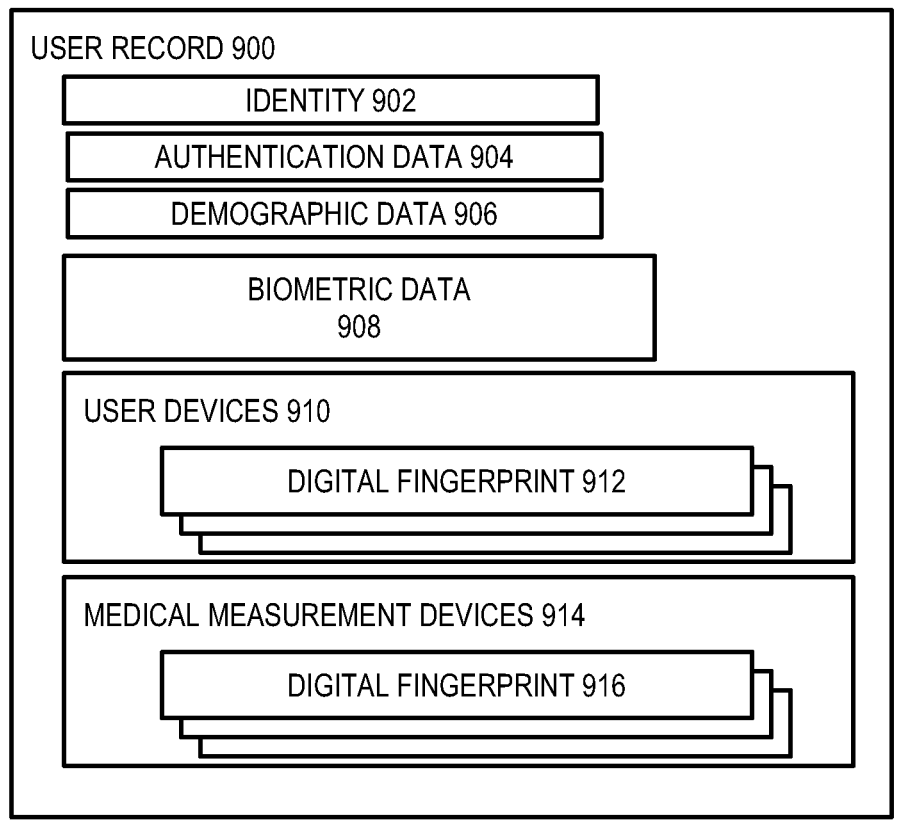
FIG. 9 is a block diagram of a user data record used by the health assessment server of FIG. 1 to assess health of a remotely located user.
Figure 10:
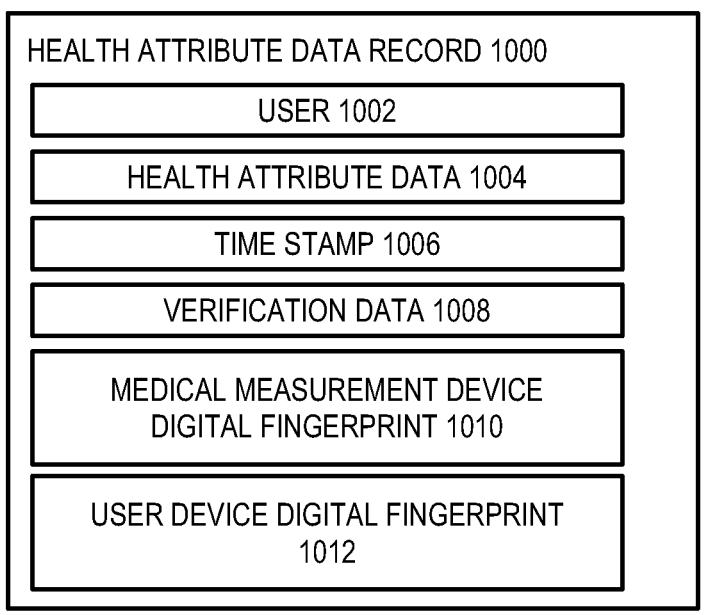
FIG. 10 is a block diagram of a health attribute data record used by the user devices and medical measurement devices of FIG. 1 to send health attribute data to health assessment server.

In step 312, policy application logic 824 (FIG. 8) forms a record for the user in users 840, e.g., a user record 900 (FIG. 9).

User record 900 includes an identity 902, authentication data 904, demographic data 906, health attribute data 908, user devices 910, and medical measurement devices 912.

Identity 902, authentication data 904, and demographic data 906 represent, respectively, the personally identifying information, authentication information, and demographic information entered by the user in step 306 (FIG. 3) and received in step 310.

Health attribute data 908 represents physical characteristics of the user as measured by medical measurement devices 104A-D. Initially, health attribute data 908 is empty in this illustrative embodiment.

User devices 910 includes digital fingerprints 912 of one or more user devices, such as user devices 102A-B, from which biometric information about the user is accepted. Biometric information received from other user devices is not accepted by health assessment server 110 as authentic.

Medical measurement devices 912 includes digital fingerprints 916 of one or more medical measurement devices assigned to the user and from which biometric information about the user is accepted. Biometric information of the user measured by other medical measurement devices is not accepted by health assessment server 110 as authentic.

In step 314 (FIG. 3), policy application logic 824 binds one or more medical measurement devices to the user, more specifically to the user devices of the user in this illustrative embodiment. Policy application logic 824 binds medical measurement device 104A (FIG. 7) to the user by storing in allowed user devices 742 digital fingerprints 912 (FIG. 9) of all user devices associated with the user. As described more completely below, such binding limits cooperation of medical measurement device 104A to only the user devices represented in user devices 910 of user record 900 and thereby associates those devices with the user.

It should be appreciated that, unless otherwise described herein, medical measurement devices 104A-D are analogous to one another and the description of any of medical measurement devices 104A-D is equally applicable to all of medical measurement devices 104A-D. Generally, each of medical measurement devices 104A-D measures a different, respective group of physical characteristics of the user but processes and reports the measurements in analogous manners. For example, medical measurement device 104A is shown to be a wrist-band heart rate monitor; medical measurement device 104B is shown to be a wrist-band blood pressure monitor; medical measurement device 104C is shown to be a blood glucose meter; and medical measurement device 104D is shown to be a digital scale that measures body fat or percent body fat. Other medical measurement devices can be used as well.

For example, to bind medical measurement device 104A to the user of user devices 102A-B, policy application logic 824 sends user devices 910 (FIG. 9) of user record 900 to medical measurement device 104A in such a way that causes communications logic 722 (FIG. 7) of medical measurement device 104A to store user devices 910 into allowed user devices 742.

In step 316 (FIG. 3), health assessment server 110 sends medical measurement devices 104A-B to the user. In this illustrative embodiment, policy application logic 824 issues an order to physically package medical measurement devices 104A-B and to ship them to an address associated with the user.

Figure 4:
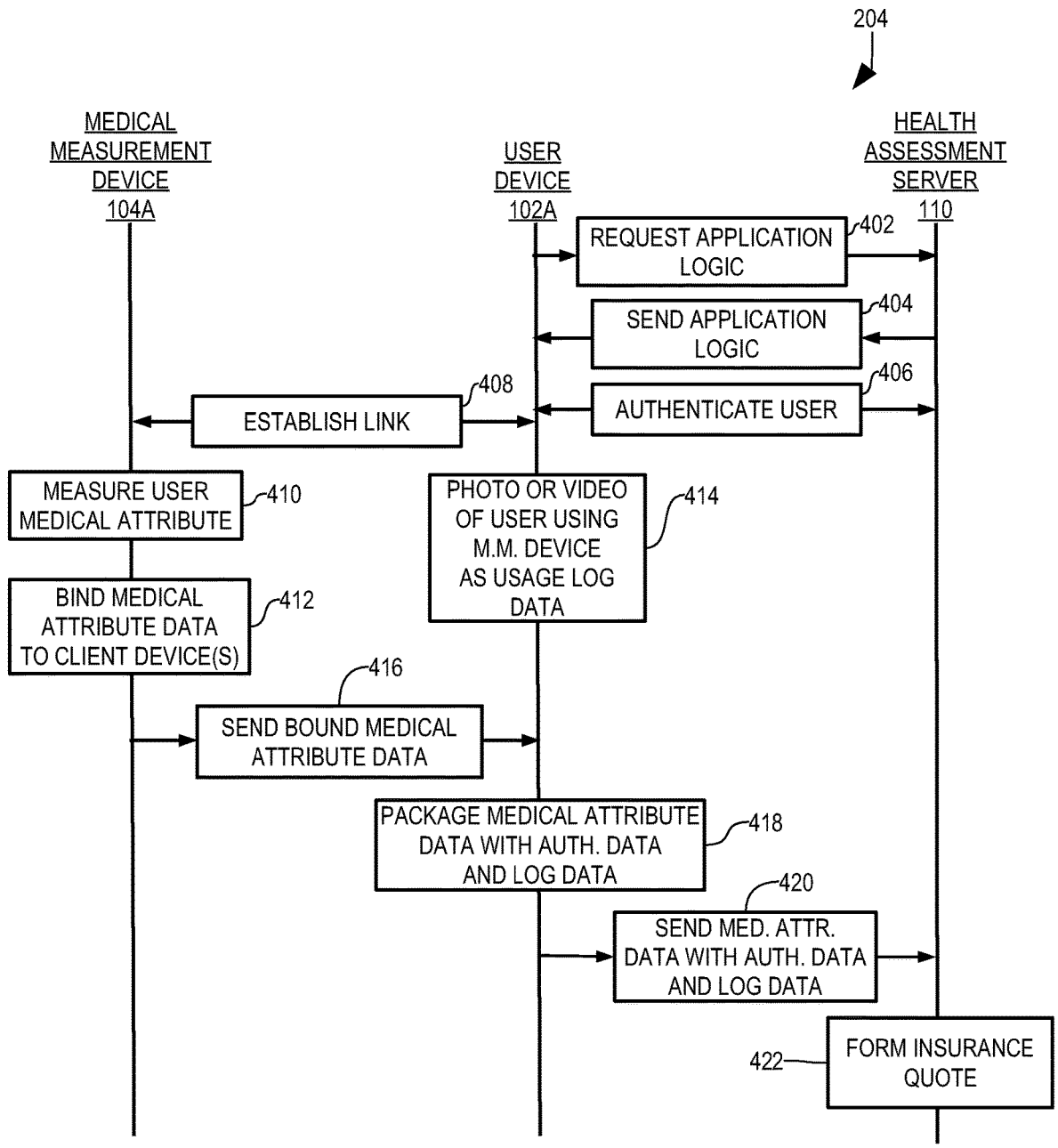

Step 204 (FIG. 2), in which health assessment server 110 coordinates with user devices 102A-B and medical measurement devices 104A-D to perform an initial assessment of the user's health, is shown in greater detail as transaction flow diagram 204 (FIG. 4).

In step 402, the user of user device 102A requests insurance application logic from health assessment server 110. The user can make the request in any of a number of ways. Since health measurement devices 104A-D (FIG. 1) are sent to the user in step 316 (FIG. 3) in response to personal and authentication information sent by the user in step 310, medical measurement devices 104A-D can be accompanied by information as to how the user can go about requesting activation of medical measurement devices 104A-D for furtherance of the insurance application process.

Figure 6:
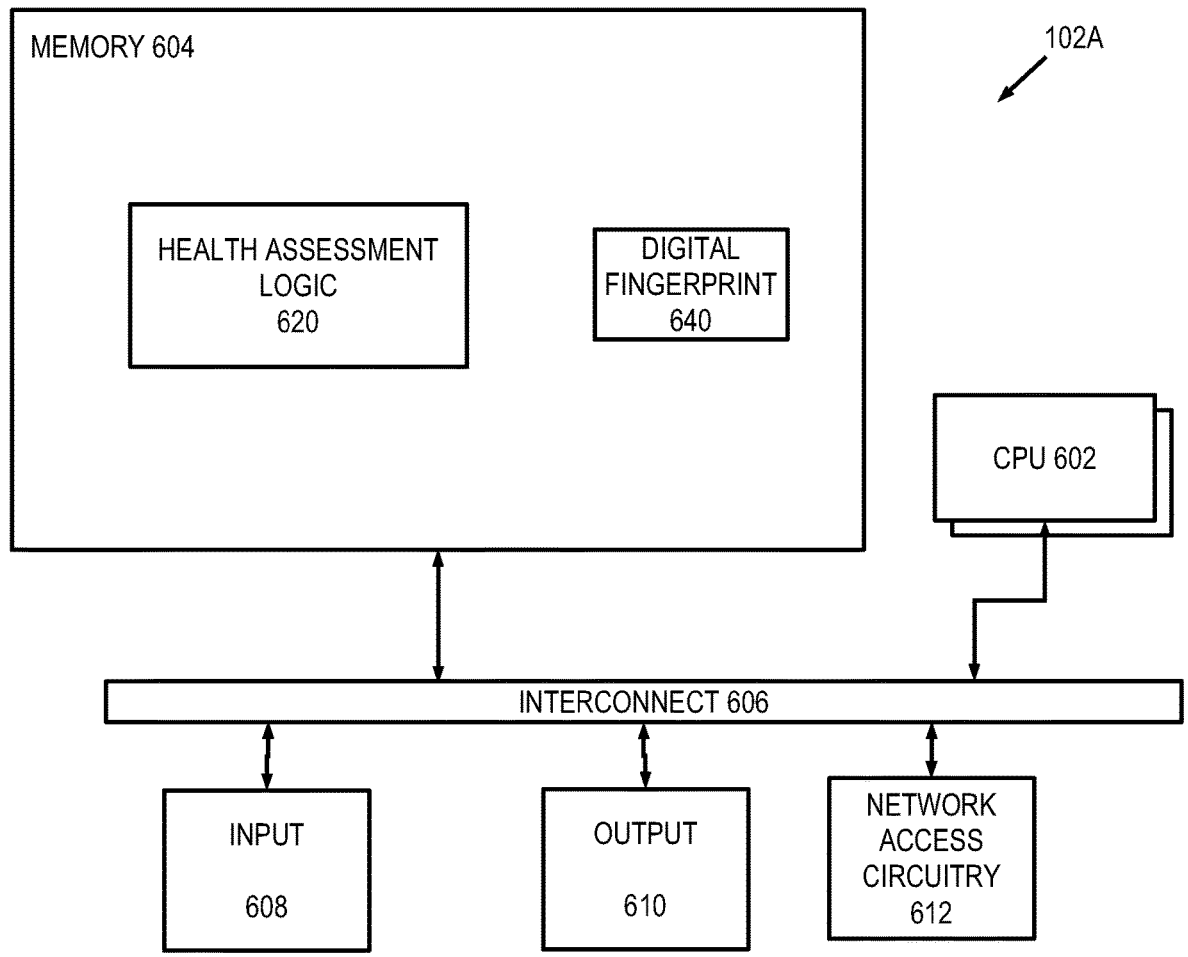
FIG. 6 is a block diagram showing a user device of FIG. 1 in greater detail.

In response to the request, health assessment server 110 sends the insurance application logic in step 404. User device 102A adds the insurance application logic to health assessment logic 620 (FIG. 6).

In step 406 (FIG. 4), health assessment logic 620 of user device 102A and authentication logic 822 (FIG. 8) of health assessment server 110 cooperate to authenticate the user, typically involving physical manipulation of one or more user input devices 608 (FIG. 6) by the user to generate signals representing authentication data corresponding to that entered by the user in step 306 (FIG. 3).

In step 408 (FIG. 4), health assessment logic 620 of user device 102A establishes a communications link with communications logic 722 (FIG. 7) of health measurement device 104A. The connection can be established through LAN 106 or through a direct connection between user device 102A and health measurement device 104A, whether wired (e.g., USB) or wireless (e.g., Bluetooth®).

Once the communications link is established in step 408, health assessment logic 620 (FIG. 6) of user device 102A and health attribute measurement logic 720 (FIG. 7) of health measurement device 104A cooperate to measure various health attributes of the user without intervention by any human being other than the user. Accordingly, the physical examination can be performed in complete privacy.

In step 410 (FIG. 4), health attribute measurement logic 720 (FIG. 7) measures one or more health attributes of the user. For example, in the case of a wrist-band heart rate monitor, health attribute measurement logic 720 can measure and log the heart rate of the user. In some instances, health assessment logic 620 (FIG. 6) prompts the user to use a particular health measurement device, e.g., by using user output devices 610 to instruct the user to step on a body fat measuring scale or to use a wrist-band blood pressure monitor or a blood glucose meter. The manner in which health attribute measurement logic 720 (FIG. 7) measures health attributes of the user can be conventional.

In some embodiments, health attribute measurement logic 720 includes time stamp data with the measured health attributes such that the time at which the health attributes were measured is known. The clock of medical measurement device 104A can be synchronized with the clock of user device 102A during step 408 in a conventional manner. Alternatively, the clocks of both medical measurement device 104A and user device 102A can be synchronized with NTP servers in a conventional manner.

In step 412, health attribute measurement logic 720 binds data representing the measured health attributes to user devices 102A-B. Such binding can be accomplished in a number of ways. For example, a data structure including both the data representing the measured health attributes and allowed user devices 742 can be cryptographically signed by health attribute measurement logic 720, thereby making the data structure tamper-evident. Alternatively, the measured health attributes can be encrypted using a private key of the user such that only the user can decrypt the measured health data attributes using a corresponding public key and public-key infrastructure (PKI). The binding of the measured health data attributes discourages fraud and, in particular, discourages use of medical measurement device 104A by someone other than the user.

Step 414 is performed by health assessment logic 620 (FIG. 6) of user device 102A asynchronously and, in some embodiments, concurrently with step 410 (FIG. 4). In step 414, health assessment logic 620 logs usage of medical measurement device 104A by the user. In one embodiment, health assessment logic 620 records video or one or more photos of the user using medical measurement device 104A using a camera that is included in user input devices 608. In an alternative embodiment, health assessment logic 620 can log interactions between user device 102A and health measurement device 104A through the link established in step 408 (FIG. 4) from operating system logs of user device 102A.

In step 416, health attribute measurement logic 720 sends the health attribute data measured in step 410 and bound in step 412 to user device 102A.

In step 418, health assessment logic 620 (FIG. 6) packages the health attribute data received in step 410 and bound in step 412 with authentication data of the user and log data collected in step 414. To the extent the health attribute data is encrypted for the user or either of user devices 102A-B, health assessment logic 620 decrypts the health attribute data such that it is readable for health assessment server 110. The authentication data can be authentication data entered by the user by which the user is authenticated or, alternatively, can be digital fingerprint 640 of user device 102A.

The time stamps in the health attribute data gathered in step 410 and the time stamps in the log data gathered in step 414 allow health assessment server 110 to verify that the health attributed were measured concurrently with use of user device 102A. In some embodiment, e.g., in which the log data includes photos and/or video of the user using medical measurement device 104A, the log data clearly identifies the user.

In step 420, health assessment logic 620 sends the packaged data of step 418 to health assessment server 110.

It should be appreciated that a full health assessment of the user can require measurement of health attributes by more than just health measurement device 104A. Accordingly, steps 408-416 are repeated for each of health measurement devices 104A-D. The application logic received in step 404 directs the user to use each of a number of health measurement devices 104A-D. The data packaged in step 418 and sent in step 420 includes measured health attributes received from all health measurement devices used by the user and all corresponding log data.

It should also be appreciated that use of two or more of medical measurement devices 104A-D can be concurrent and that use of any of medical measurement devices 104A-D can be extended. For example, health assessment logic 620 can direct the user to wear a heart rate monitor and a pedometer for an extended period of several days or longer. Health assessment logic 620 can also direct the user to measure blood pressure, blood glucose, body fat, and/or weight while continuing to wear the heart rate monitor and the pedometer.

In step 422, health insurance logic 820 (FIG. 8) forms an insurance quote from the received packaged data. In particular, authentication logic 822 verifies the authenticity of the user and user device 102A from which the packaged data is received. In addition, authentication logic 822 compares time stamps in the measured health attribute data and in the log data to verify that health measurement devices 104A-D and user device 102A were used concurrently. If authentication logic 822 detects a possible discrepancy, authentication logic 822 can flag the current application for review by human quality-control personnel. In addition, authentication logic 822 can include facial recognition logic to compare facial features in photos or video of use of medical measurement devices 104A-D to facial features in a photo included in the authentication data originally provided by the user.

Once the data is authenticated, health assessment logic 828 can analyze and classify measured health attribute data to summarize the health of the user.

Policy pricing logic 832 uses the analyzed and classified measured health attribute data and actuarial data 844 to determine insurance premium prices to offer to the user. Use of health assessments and actuarial data to determine insurance premium prices to offer to an applicant, while complex, is known and not described herein.

Of course, the insurance premium prices are communicated to the user and the user is offered the opportunity to purchase insurance under those terms.

The user's experience in this system is very convenient and very private. Textual portions of the insurance application are entered through a computer network from any location convenient to the user. Soon thereafter, the user receives medical measurement devices to complete portions of the insurance application that require physical examination. The user is examined by herself on her own time in a place of her choosing. The examination can be conducted at any time and in complete privacy. In effect, the user's experience is physical self-examination "in a box".

In addition, the physical examination communicates measured health attributes to user device 102A immediately. In some embodiments, the complete package of measured health attributes can be sent to health assessment server 110 as soon as the final measurement is taken and communicated to user device 102A, without intervention by the user. In other embodiments, steps 418 and 420 can be repeated for each medical measurement device and the user can be immediately informed if there is a problem with any measurements and directed to repeat those measurements.

Moreover, the user receives a quote for insurance coverage almost immediately following the physical self-examination.

As noted above, initial health assessment is not the end. In step 206 (FIG. 2), health assessment server 110 coordinates with user devices 102A-B and medical measurement devices 104A-D to perform periodic health maintenance of the user. In particular, health monitoring logic 826 (FIG. 8) engages the user to performance periodic health maintenance and reassessment. The user can agree to such a maintenance program in any of a number of ways. For example, health assessment server 110 can offer such a service to the user and the user can actively accept the offer using conventional user interface techniques. Alternatively, health assessment server 110 can be configured to require such health maintenance of all insured users.

Figure 5:
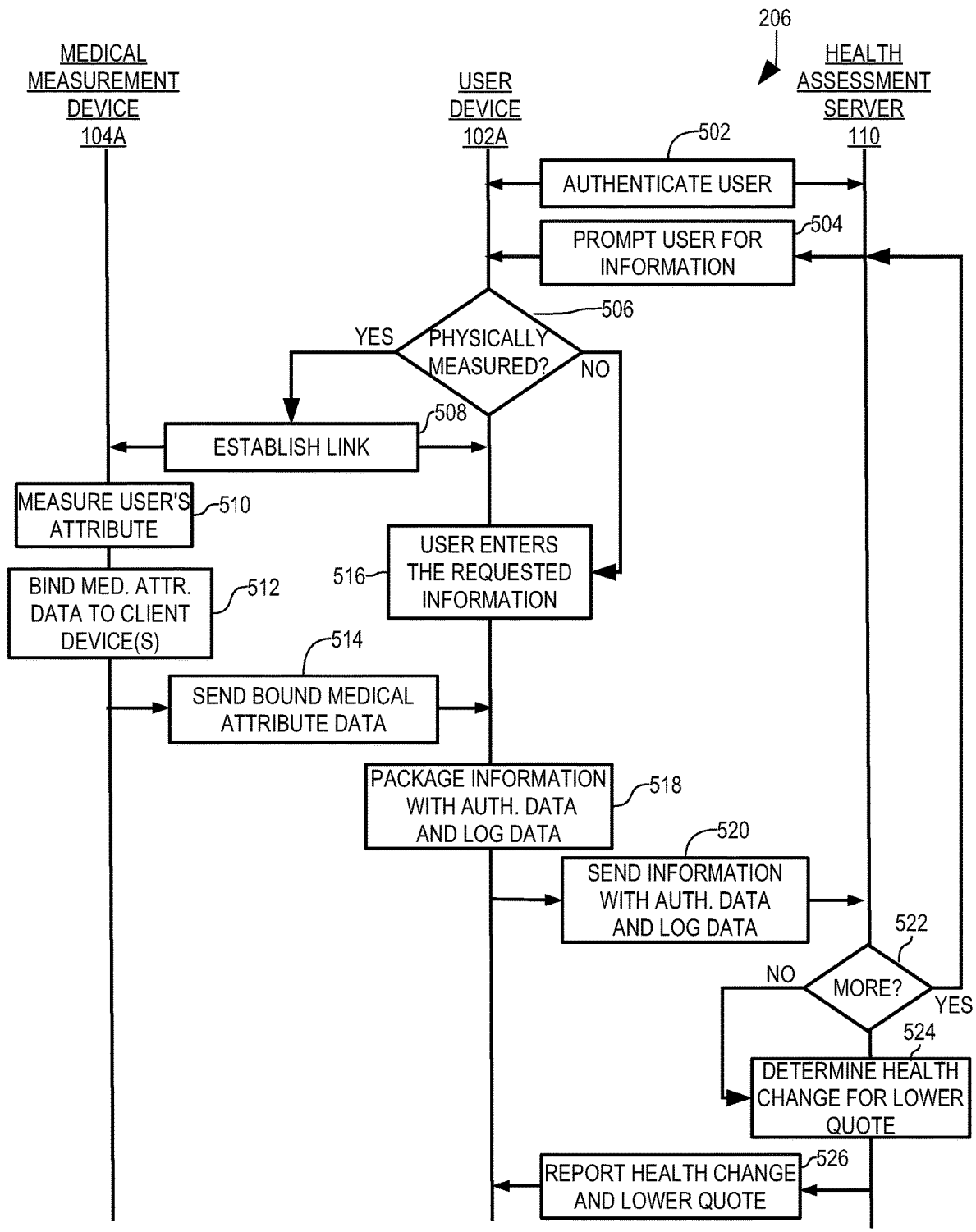

Step 206 (FIG. 2), is shown in greater detail as transaction flow diagram 206 (FIG. 5). In step 502, authentication logic 822 (FIG. 8) of health assessment server 110 authenticates the user of user device 102A in the manner described above with respect to step 402 (FIG. 4).

Figure 11:
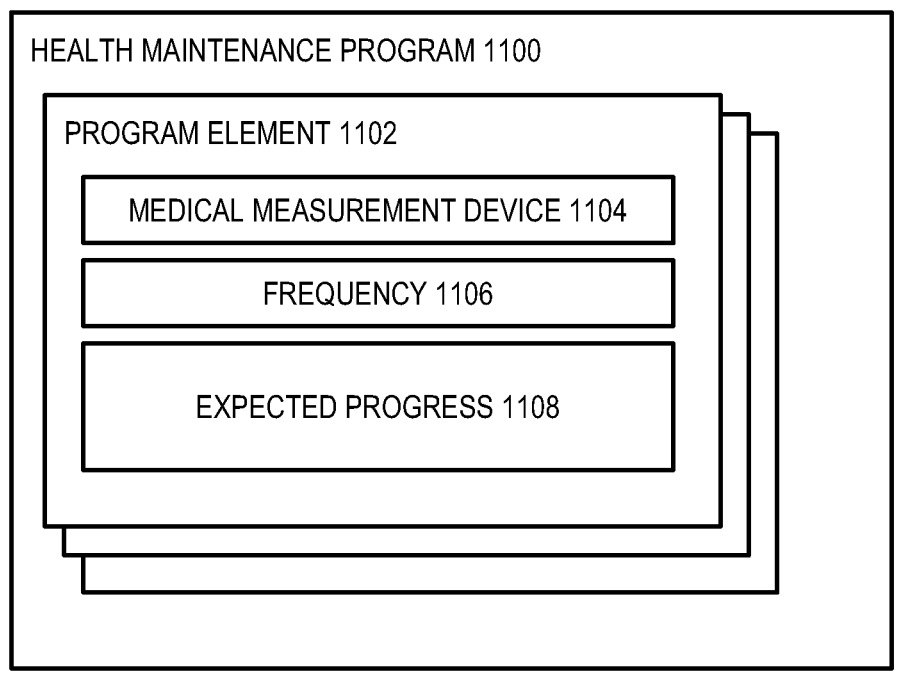
FIG. 11 is a block diagram of a health maintenance program used by the health assessment server to direct the user to use the user devices and the medical measurement devices in a health maintenance or health improvement course of action.

In step 504, health monitoring logic 826 (FIG. 8) prompts the user for information regarding a maintenance health assessment. Health monitoring logic 826 implements one or more health maintenance programs of the general structure shown in FIG. 11. Health maintenance program 1100 includes one or more program elements 1102, each of which includes a medical measurement device 1104, a frequency 1106, and expected progress 1108. Medical measurement device 1104 is data identifying a particular type of medical measurement device or can identify a specific one of medical measurement devices 104A-D. Frequency 1106 is data specifying a frequency and duration of use of the medical measurement device identified by medical measurement device 1104. Expected progress 1108 is data specifying a degree or type of progress in the health attributes measured by the subject medical measurement device that health maintenance program 1100 intends to achieve.

The specific details of a given health program depend on the progress to be achieved and current scientific and medical thinking as to how such progress is to be achieved. Example programs include weight loss programs, smoking cessation programs, alcohol and drug abstinence programs, and fitness programs. Health maintenance program 1100 indicates which health attributes are to be measured at a given time, based on frequency 1104 of the various elements. Health monitoring logic 826 (FIG. 8) directs the user to provide such measurements for a given program element in step 504 (FIG. 5).

In test step 506, health assessment logic 620 (FIG. 6) determines whether the requested physical attribute information is physically measured, i.e., whether any of medical measurement devices 104A-D are required to measure physical attributes of the user. In some health maintenance programs, the user is required to enter information that is not readily measurable by medical measurement devices 104A-D. For example, the user may be required to enter data specifying foods and beverages the user has consumed in a weight loss program. If no medical measurement device is required for a program element, medical measurement device 1104 so indicates and indicates the type of information to be entered by the user.

If the requested physical attribute information is physically measured, processing by health assessment logic 620 transfers to steps 508, 510, 512, and 514, which are directly analogous to steps 408 (FIG. 4), 410, 412, and 416, respectively. Conversely, if the requested physical attribute information is not physically measured, processing by health assessment logic 620 transfers to step 516 (FIG. 5) in which the user enters the requested information using conventional user interface techniques.

In steps 518 and 520, health assessment logic 620 packages the collected information and authentication and log data and sends the packaged data to health assessment server 110 in the manner described above with respect to steps 418 (FIG. 4) and 420, respectively.

In step 520 (FIG. 5), health monitoring logic 826 (FIG. 8) determines whether health maintenance program 1100 has additional program elements that have not yet been satisfied by the user. If so, processing transfers to step 504 in which the next program element of health maintenance program 1100 is processed according to steps 504-520.

Once all of program elements 1102 of health maintenance program 1100 have been processed according to steps 504-520 (FIG. 5), processing by health monitoring logic 826 transfers to step 524.

In step 524, health monitoring logic 826 (FIG. 8) causes policy pricing logic 832 to identify one or more health states at which insurance premiums would be priced less than the price currently paid by the user.

For each such health state, health monitoring logic 826 projects a time at which the health state can be achieved by the user, using expected progress 1108 of various program elements of a health maintenance program such as health maintenance program 1100.

In step 526 (FIG. 5), health monitoring logic 826 (FIG. 8) reports to the user changes in her health status and reduced premiums associated with the changes. For example, health monitoring logic 826 can report that the user can save 10% on her life insurance premiums if she loses 20 pounds or can save 20% on her life insurance premiums if she quits smoking. Using progress achieved by the user to date in the health maintenance program and expected progress 1108 for the various elements of the program, health monitoring logic 826 reports progress toward a health state with a lower insurance premium. For example, health monitoring logic 826 can report that, given progress so far, the user can lower her life insurance premiums in two months.

User device 102A is shown in greater detail in FIG. 6. User device 102A includes one or more microprocessors 602 (collectively referred to as CPU 602) that retrieve data and/or instructions from memory 604 and execute retrieved instructions in a conventional manner. Memory 604 can include generally any computer-readable medium including, for example, persistent memory such as magnetic and/or optical disks, ROM, and PROM and volatile memory such as RAM.

CPU 602 and memory 604 are connected to one another through a conventional interconnect 606, which is a bus in this illustrative embodiment and which connects CPU 602 and memory 604 to one or more input devices 608, output devices 610, and network access circuitry 612. Input devices 608 can include, for example, a keyboard, a keypad, a touch-sensitive screen, a mouse, a microphone, and one or more cameras. Output devices 610 can include, for example, a display—such as a liquid crystal display (LCD)—and one or more loudspeakers. Network access circuitry 612 sends and receives data through computer networks such as local area network 112 (FIG. 1), the Internet, and mobile device data networks, for example. In some embodiments, input devices 608 and output devices 610 can be omitted.

A number of components of user device 102A are stored in memory 604. In particular, health assessment logic 620 is all or part of one or more computer processes executing within CPU 602 from memory 604 in this illustrative embodiment but can also be implemented using digital logic circuitry. As used herein, "logic" refers to (i) logic implemented as computer instructions and/or data within one or more computer processes and/or (ii) logic implemented in electronic circuitry. Digital fingerprint 640 is data stored persistently in memory 604.

Figure 7:
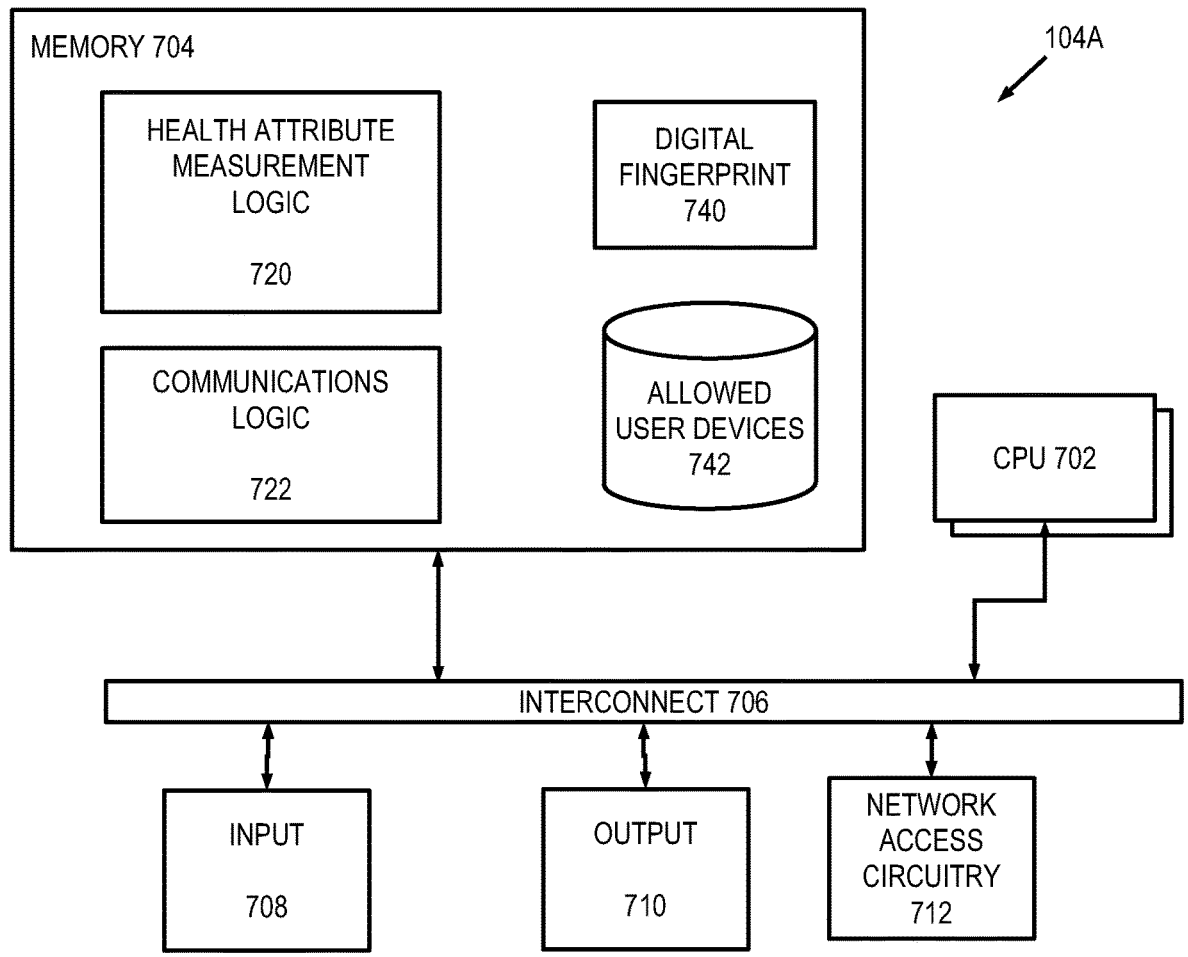
FIG. 7 is a block diagram showing a medical measurement device of FIG. 1 in greater detail.

Medical measurement device 104A is shown in greater detail in FIG. 7. Medical measurement device 104A includes one or more microprocessors 702 (collectively referred to as CPU 702), memory 704, an interconnect 706, input devices 708, output devices 710, network access circuitry 712 that are directly analogous to CPU 602 (FIG. 6), memory 604, an interconnect 606, input devices 608, output devices 610, network access circuitry 612, respectively. Network access circuitry 712 sends and receives data through computer networks such as local area network 106 (FIG. 1) and the Internet for example.

A number of components of medical measurement device 104A are stored in memory 704. In particular, health attribute measurement logic 720 and communications logic 722 are each all or part of one or more computer processes executing within CPU 702 from memory 704 in this illustrative embodiment but can also be implemented using digital logic circuitry. Digital fingerprint 740 and allowed user devices 742 are data stored persistently in memory 704. In this illustrative embodiment, allowed user devices 742 is organized as one or more databases.

Health assessment server 110 is shown in greater detail in FIG. 8. Health assessment server 110 includes one or more microprocessors 802 (collectively referred to as CPU 802), memory 804, an interconnect 806, input devices 808, output devices 810, network access circuitry 812 that are directly analogous to CPU 602 (FIG. 6), memory 604, an interconnect 606, input devices 608, output devices 610, network access circuitry 612, respectively. As health assessment server 110 (FIG. 8) is a server computer, input devices 808 and output devices 810 can be omitted.

A number of components of health assessment server 110 are stored in memory 804. In particular, health insurance logic 820 is all or part of one or more computer processes executing within CPU 802 from memory 804 in this illustrative embodiment but can also be implemented using digital logic circuitry. Users 840, health measurement devices 842, and actuarial data 844 are each data stored persistently in memory 804. In this illustrative embodiment, users 840, health measurement devices 842, and actuarial data 844 are each organized as one or more databases.

The above description is illustrative only and is not limiting. The present invention is defined solely by the claims which follow and their full range of equivalents. It is intended that the following appended claims be interpreted as including all such alterations, modifications, permutations, and substitute equivalents as fall within the true spirit and scope of the present invention.

What is claimed is:
1. A computer system, comprising:
   at least one processor;
   a computer readable medium that is operatively coupled to the processor; and
   logic stored in the computer readable medium that when executed by the processor causes the computer system to perform the following steps:

binding one or more medical measurement devices to one or more user devices that are under control and operation of the person;

receiving health attribute data from the medical measurement devices through a computer network, wherein the health attribute data represents one or more health attributes of the person measured by the medical measurement devices;

receiving log data from one or more selected ones of the user devices, wherein the log data represents events (i) that occurred in the selected user devices and (ii) that are associated with the usage of the medical measurement devices;

comparing the health attribute data and the log data to determine that the medical measurement devices measured the health attributes of the person concurrently with the person's use of the selected user devices; and using the health attribute data to assess a health state of the person;

wherein said binding step is accomplished by encrypting the health attribute data using a private key of the person.

2. The computer system of claim 1 wherein the logic when executed by the processor further causes the computer system to perform the steps of:

determining an improved heath state at which insurance benefits accrue to the person; and reporting the improved health state and the benefits to the person.

3. The computer system of claim 2 wherein the logic when executed by the processor further causes the computer system to perform the steps of:

repeating (i) the receiving health attribute data, (ii) the receiving log data, and (iii) the comparing;

using new health attribute data resulting from the repetition of the receiving health attribute data to assess a new health state of the person;

comparing the health state, the new health state, and the improved health state to determine progress toward the improved health state; and reporting the progress to the user.

4. The computer system of claim 1 wherein the logic when executed by the processor further causes the computer system to perform the steps of:

determining an improved health state at which insurance benefits accrue to the person; and reporting the improved health state and the benefits to the person.

5. The computer system of claim 4 wherein the logic when executed by the processor further causes the computer system to perform the steps of:

repeating (i) the receiving health attribute data, (ii) the receiving log data, and (iii) the comparing;

using new health attribute data resulting from the repetition of the receiving health attribute data to assess a new health state of the person;

comparing the health state, the new health state, and the improved health state to determine progress toward the improved health state; and reporting the progress to the user.

6. The computer system of claim 1 wherein the logic when executed by the processor further causes the computer system to perform the steps of:

determining an improved health state at which insurance benefits accrue to the person; and reporting the improved health state and the benefits to the person.

7. The computer system of claim 6 wherein the logic when executed by the processor further causes the computer system to perform the steps of:

repeating (i) the receiving health attribute data, (ii) the receiving log data, and (iii) the comparing;

using new health attribute data resulting from the repetition of the receiving health attribute data to assess a new health state of the person;

comparing the health state, the new health state, and the improved health state to determine progress toward the improved health state; and reporting the progress to the user.

8. A computer system for assessing the health of a person, comprising:

at least one processor;

a computer readable medium that is operatively coupled to the processor; and logic stored in the computer readable medium that when executed by the processor causes the computer system to perform the following steps:

binding one or more medical measurement devices to one or more user devices that are under control and operation of the person;

receiving health attribute data from the medical measurement devices through a computer network, wherein the health attribute data represents one or more health attributes of the person measured by the medical measurement devices;

receiving log data from one or more selected ones of the user devices, wherein the log data represents events (i) that occurred in the selected user devices and (ii) that are associated with the usage of the medical measurement devices;

comparing the health attribute data and the log data to determine that the medical measurement devices measured the health attributes of the person concurrently with the person's use of the selected user devices; and using the health attribute data to assess a health state of the person;

wherein said binding step comprises storing identifiers of the user devices in the medical measurement devices and including logic in the medical measurement devices that limits functionality of the medical measurement devices to use only in conjunction with any of the user devices.

9. The computer system of claim 8 wherein the logic when executed by the processor further causes the computer system to perform the steps of:

determining an improved health state at which insurance benefits accrue to the person; and reporting the improved health state and the benefits to the person.

10. The computer system of claim 9 wherein the logic when executed by the processor further causes the computer system to perform the steps of:

repeating (i) the receiving health attribute data, (ii) the receiving log data, and (iii) the comparing;

using new health attribute data resulting from the repetition of the receiving health attribute data to assess a new health state of the person;

comparing the health state, the new health state, and the improved health state to determine progress toward the improved health state; and reporting the progress to the user.

11. The computer system of claim 8 wherein the identifiers of the user devices are digital fingerprints of the user devices.

12. A computer readable medium encoded with instructions that when executed by a computer processor causes performance of the following steps:

binding one or more medical measurement devices to one or more user devices that are under control and operation of the person;

receiving health attribute data from the medical measurement devices through a computer network, wherein the health attribute data represents one or more health attributes of the person measured by the medical measurement devices;

receiving log data from one or more selected ones of the user devices, wherein the log data represents events (i) that occurred in the selected user devices and (ii) that are associated with the usage of the medical measurement devices;

comparing the health attribute data and the log data to determine that the medical measurement devices measured the health attributes of the person concurrently with the person's use of the selected user devices; and using the health attribute data to assess a health state of the person;

wherein said binding step is accomplished by encrypting the health attribute data using a private key of the person.

13. The computer readable medium of claim 12 encoded with further instructions that when executed by the computer processor causes performance of the following steps:

determining an improved heath state at which insurance benefits accrue to the person; and reporting the improved health state and the benefits to the person.

14. A computer readable medium encoded with instructions that when executed by a computer processor causes performance of the following steps:

binding one or more medical measurement devices to one or more user devices that are under control and operation of the person;

receiving health attribute data from the medical measurement devices through a computer network, wherein the health attribute data represents one or more health attributes of the person measured by the medical measurement devices;

receiving log data from one or more selected ones of the user devices, wherein the log data represents events (i) that occurred in the selected user devices and (ii) that are associated with the usage of the medical measurement devices;

comparing the health attribute data and the log data to determine that the medical measurement devices measured the health attributes of the person concurrently with the person's use of the selected user devices; and using the health attribute data to assess a health state of the person;

wherein said binding step comprises storing identifiers of the user devices in the medical measurement devices and including logic in the medical measurement devices that limits functionality of the medical measurement devices to use only in conjunction with any of the user devices.

\* \* \* \* \*